Figure 1:
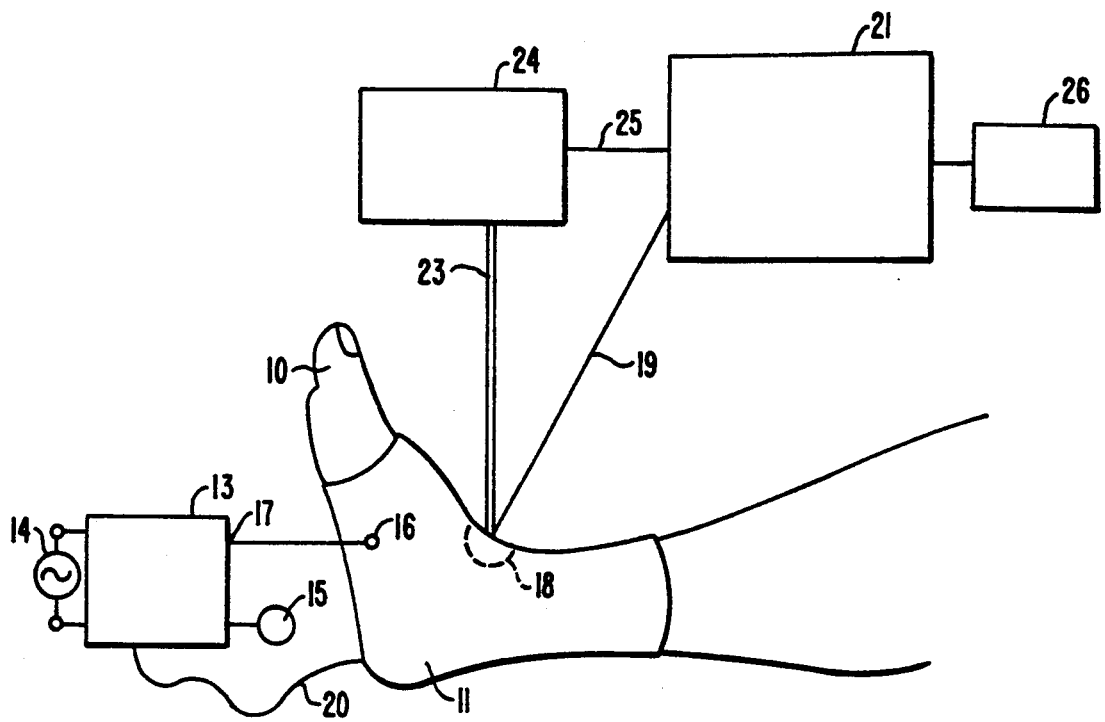

United States Patent [19]
Koltringer

[11] Patent Number: 5,293,876
[45] Date of Patent: * Mar. 15, 1994

[54] METHOD AND APPARATUS FOR THE DIAGNOSIS OF POLYNEUROPATHY SYNDROMES

[76] Inventor: Peter Koltringer, Lortzingasse 20, Graz, Austria

[*] Notice: The portion of the term of this patent subsequent to Mar. 9, 2010 has been disclaimed.

[21] Appl. No.: 781,786

[22] Filed: Oct. 23, 1991

Related U.S. Application Data

[63] Continuation of Ser. No. 445,724, Dec. 1, 1989, Pat. No. 5,191,895.

[51] Int. Cl.$^5$ .............................................. A61B 19/00
[52] U.S. Cl. ..................................... 128/736; 128/742; 374/44
[58] Field of Search ............... 128/736, 742, 691, 399; 73/202.5, 204.11, 204.23; 374/44, 54

[56] References Cited

U.S. PATENT DOCUMENTS 3,623,473 11/1971 Anderson ........................ 128/736 X
4,228,805 10/1980 Rosen et al. ..................... 128/736 X
4,653,507 3/1987 Laudadio ............................. 128/742
4,754,760 7/1988 Fukukita et al. ................ 128/736 X
4,859,078 8/1989 Bowman et al. ................ 128/736 X

FOREIGN PATENT DOCUMENTS 1168188 7/1985 U.S.S.R. ............................... 128/736
1463221 3/1989 U.S.S.R. ............................... 128/736

Primary Examiner—Peter A. Aschenbrenner
Attorney, Agent, or Firm—Townsend and Townsend Khourie and Crew

[57] ABSTRACT

A method and/or an apparatus for the determination of whether a subject has nerve damage (polyneuropathy) and/or the degree of the nerve damage is characterized in that an increase of the skin temperature is provoked at an extremity of the subject, that at the same time perfusion value or a value correlated with this perfusion value is measured at this extremity, and the time from the start of the increase in temperature of the skin up to the start of an increase in perfusion as a result of the elevated skin temperature is evaluated as a measure for the presence and/or the degree of the nerve damage.

13 Claims, 4 Drawing Sheets

TABLE 1: HYPERTHERMAL PERFUSION-LATENCY IN THE 4 GROUPS

| GROUPS: | (SEC) | SIGNIFICANCE: (p ACCORDING TO WILCOXON) (P ACCORDING TO CHI-SQUARE) | | |
|---|---|---|---|---|
| GROUP 1 (HEALTHY) | 26 (22-43) | ] $p \leq 0,01$ ($P \leq 0,0001$) | ] $p \leq 0,01$ ($P \leq 0,0001$) | |
| GROUP 2 (PARESES) | 64 (44-85) | ] $p \leq 0,01$ ($P \leq 0,0001$) | | ] $p \leq 0,01$ ($P \leq 0,0001$) |
| GROUP 3 (SENS. PNS) | 180 (160-195) | ] $p \leq 0,02$ ($P \leq 0,0001$) | ] $p \leq 0,01$ ($P \leq 0,0001$) | |
| GROUP 4 (MOT. PNS) | 235 (181-280) | | | |

FIG. 3A.

TABLE 2: INITIAL PERFUSION IN THE 4 GROUPS (GIVEN IN PERFUSION UNITS)

| GROUPS: | INITIAL PERFUSION | SIGNIFICANCE: (p ACCORDING TO WILCOXON) (P ACCORDING TO CHI-SQUARE) |
|---|---|---|
| GROUP 1 (HEALTHY) | 5,8 (3,3-6,5) | ] ] ] p AND P NOT SIGNIFICANT |
| GROUP 2 (PARESES) | 7,8 (5,2-8,1) | |
| GROUP 3 (SENS. PNS) | 4,7 (4,1-5,2) | |
| GROUP 4 (MOT. PNS) | 4,3 (3,6-5,0) | |

FIG. 3B.

TABLE 3: MAXIMUM PERFUSION IN THE 4 GROUPS (GIVEN IN PERFUSION UNITS)

| GROUPS: | MAXIMUM PERFUSION | SIGNIFICANCE: (p ACCORDING TO WILCOXON) (P ACCORDING TO CHI-SQUARE) | | |
|---|---|---|---|---|
| GROUP 1 (HEALTHY) | 8,8 (5,8-14,2) | ] p:n.s. (P:n.s.) | ] $p \leq 0,02$ (P:n.s.) | |
| GROUP 2 (PARESES) | 9,1 (8,1-10,3) | ] $p \leq 0,01$ ($P \leq 0,0001$) | | ] $p < 0,01$ (P:n.s.) |
| GROUP 3 (SENS. PNS) | 5,6 (4,7-6,3) | ] $p \leq 0,02$ ($P \leq 0,0001$) | ] $p \leq 0,01$ ($P \leq 0,0001$) | |
| GROUP 4 (MOT. PNS) | 4,6 (4,1-5,2) | | | |

FIG. 3C.

METHOD AND APPARATUS FOR THE DIAGNOSIS OF POLYNEUROPATHY SYNDROMES

This is a continuation of application Ser. No. 07/445,724, filed Dec. 1, 1989, now U.S. Pat. No. 5,191,895.

The present invention relates to a method and an apparatus for determining whether a subject has nerve damage (polyneuropathy) and/or the degree of the nerve damage.

With numerous diseases polyneuropathy syndrom (PNS) arises as a frequent complication. Above all diabetes mellitus should be named here. In an extensive investigation by Canal et al. (Canal N, Pozza G(eds): Peripheral neuropathies. Elsevier North-Holland, Amsterdam, pages 247 to 255) it was found that after a period of more than five years for patients requiring insulin for diabetes mellitus only 18% were still not suffering from a manifest polyneuropathy syndrome. As further frequent causes consideration should be paid, above all, to other metabolic disturbances, such as for example in the context of chronic alcoholism (ethylismus) with various poisons or also neoplastic and inflamatory processes.

The clinical study of PNS is very diverse and numerous subdivisions have been proposed in recent years (Brown M. J., Asbury A. K. (1984) Diabetic neuropathy. Ann.Neurol 15: 2-12). The customary course shows generally a start at the lower extremities in the form of painful malsensations which initially occur primarily at night. In further succession sock-like and glove-like sensibility disturbances, loss of depth of sensitivity, areflexia starting with the achilles cord reflex and finally pareses should be named, of which the most frequent is the peroneal paresis.

As a result of this diversity of symptoms which mainly occur in combined form with different dominance numerous attempts have also been made to objectify the PNS in the last three decades, see for example Hoffmann A., Conen D., Leibundgut U., Berger W. (1982) A skin test for automatic neuropathy. Eur Neurol 21: 29-33; Kennedy W. R., Sakuda M. Sutherland D. Goetz F. C. (1984) The sweating deficiency in diabetes mellitus: methods of quantification and clinical correlation. Neurology 34: 758-763; and Ward J. D., Fisher D. J., Barnes C. G., Jessop J. D. (1971) Improvement in nerve conduction following treatment in newly diagnosed diabetes. Lancet i: 428). As one of the few investigations which can be carried out routinely there remains the measurement of the motoric nerve conduction speed by Ward et al which takes place in the clinical routine at the nervus peronaeus since this is the nerve which is most frequently affected. This diagnostic route however mainly only shows changes when severe disturbances are already present. However it is precisely at this stage that the possibilities of therapy are no longer satisfactory.

The object of the present invention is thus to propose a diagnostic method and an apparatus for carrying out this method which makes it possible to recognise neuropathic or polyneuropathic changes at an early stage, which can be carried out and used in routine operation and which thus makes a timely therapeutic treatment of the neuropathy possible. Furthermore the method and apparatus should make it possible to achieve an objective judgement of the pain sensed by the patient.

The present invention starts from the consideration that the autonomous nerve fibers are generally also affected at a very early stage with polyneuropathic changes, so that it should be possible to detect the state of the autonomous nerve fibers via a possible dysfunction of the skin. Thereafter it was speculated that a dysfunction of the skin could eventually be determined by a change in the microcirculation.

After carrying out microcirculation measurements with several subjects having different stages of polyneuropathic diseases it was however determined that the perfusion values which were found suffers from a very large scatter and that no evaluatable correlation was present with the degree of the illness. It was then however surprisingly found that on heating the skin of the individual subject in order to provoke an increase of the microcirculation the time from the increase of the skin temperature up to the start of the increase of perfusion had a very reliable correlation with the state of illness found by other methods. The measured time, termed the "hyperthermal perfusion-latency" thus forms a reliable measurement method for determining whether nerve damage is present and the degree of this nerve damage. The hyperthermal perfusion-latency is larger the more severe the nerve damage is at the vessels of the extremity (component of the so-called "autonomous nerve system"). It was thus found that with severe polyneuropathic syndroms no rise in perfusion could be found at all. The hyperthermal perfusion-latency is therefore also no longer measurable there since the perfusion remains at the initial level. This result is however also of significance since one has in this way a confirmation that nerve damage of the most severe degree is present.

Particularly preferred embodiments of the method of the invention and of the apparatus of the invention can be found from the subordinate claims.

Particularly advantageous is above all the apparatus of the present invention where a computer is used for determining and evaluating the hyperthermal perfusion-latency and for producing a protocol concerning the measurement which has been carried out. In this way the possibility exists of carrying out the measurements with relatively untrained personnel and observing the state of a particular patient over a long period of time, thus determining the course of his illness and the therapeutic success by a comparison of the protocols taken over a long period of time on different days. This long term evaluation can also be effected by the computer.

It is particular advantageous with the method and apparatus of the invention that the measurement can be carried out rapidly and without pain for the patient, with the result being extremely reliable and providing a reliable result even at a very early stage of a poloneuropathy, so that a start can be made at an early stage with the therapeutic treatment of the polyneuropathy.

A related, however alternative solution of the initially set task is also provided.

These alternative solutions are based on the recognition that the increase in temperature of the skin in the region of the heated extremity, but at a position which is not directly heated, is correlated with the perfusion values at or near this position since an increase of the perfusion can be equated with an increase of the heat transport by the blood and thus also with a change in temperature.

A statistical analysis of values measured on subjects has clearly established the correlation.

Advantageous further developments of this alternative solution are also provided by the present invention.

Figure 2:
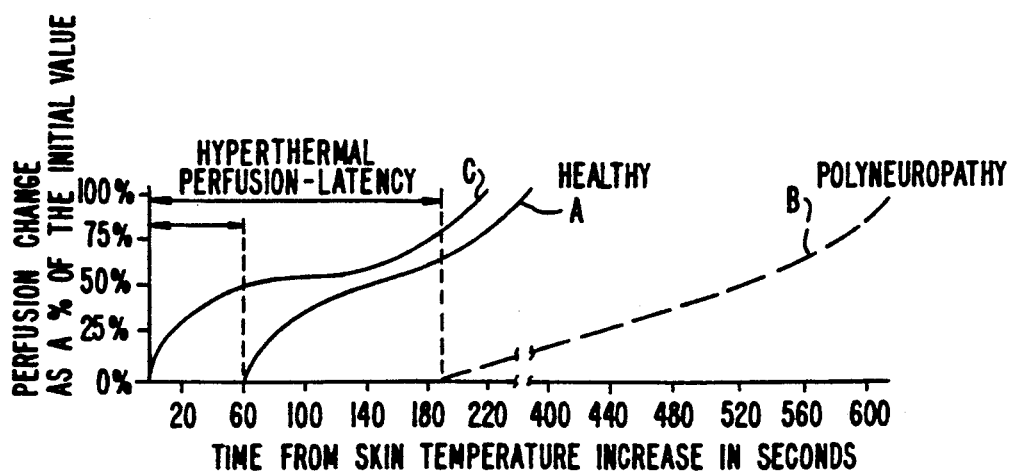
Figure 4A:
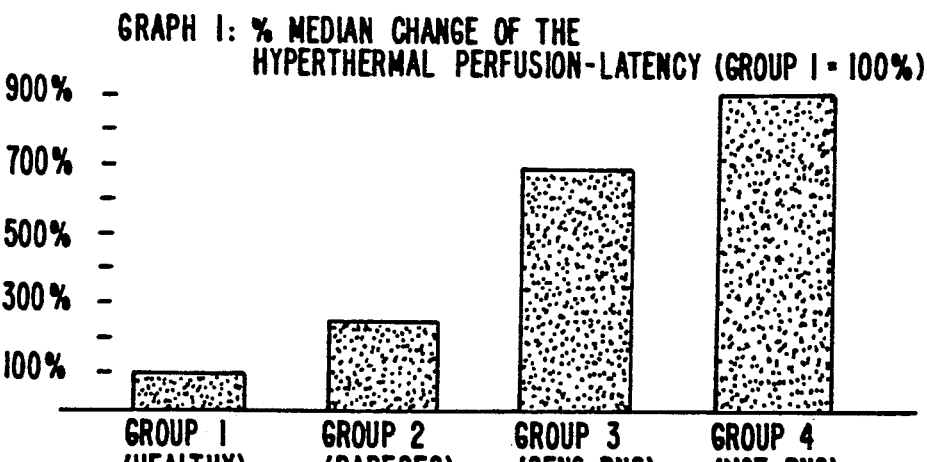
Figure 4B:
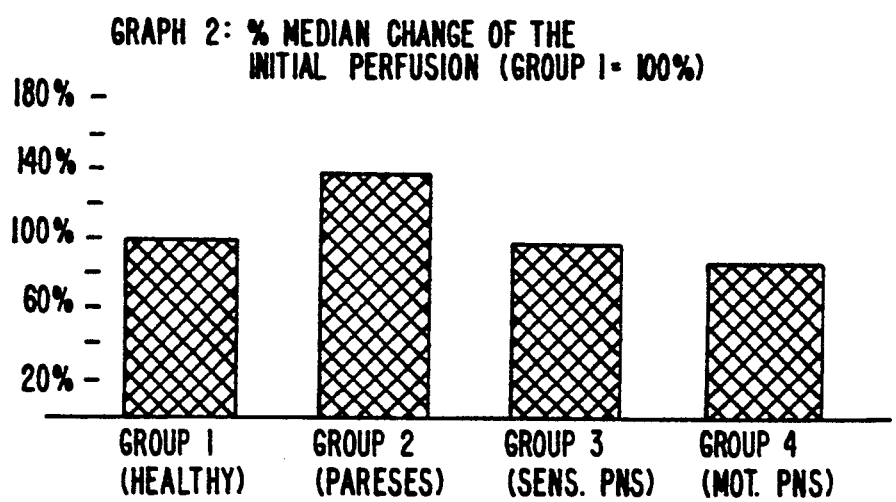
Figure 4C:
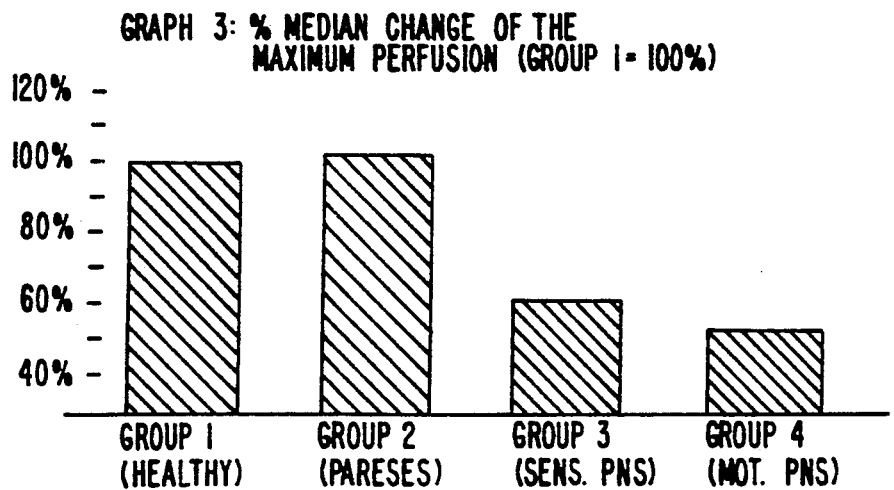
Figure 5:
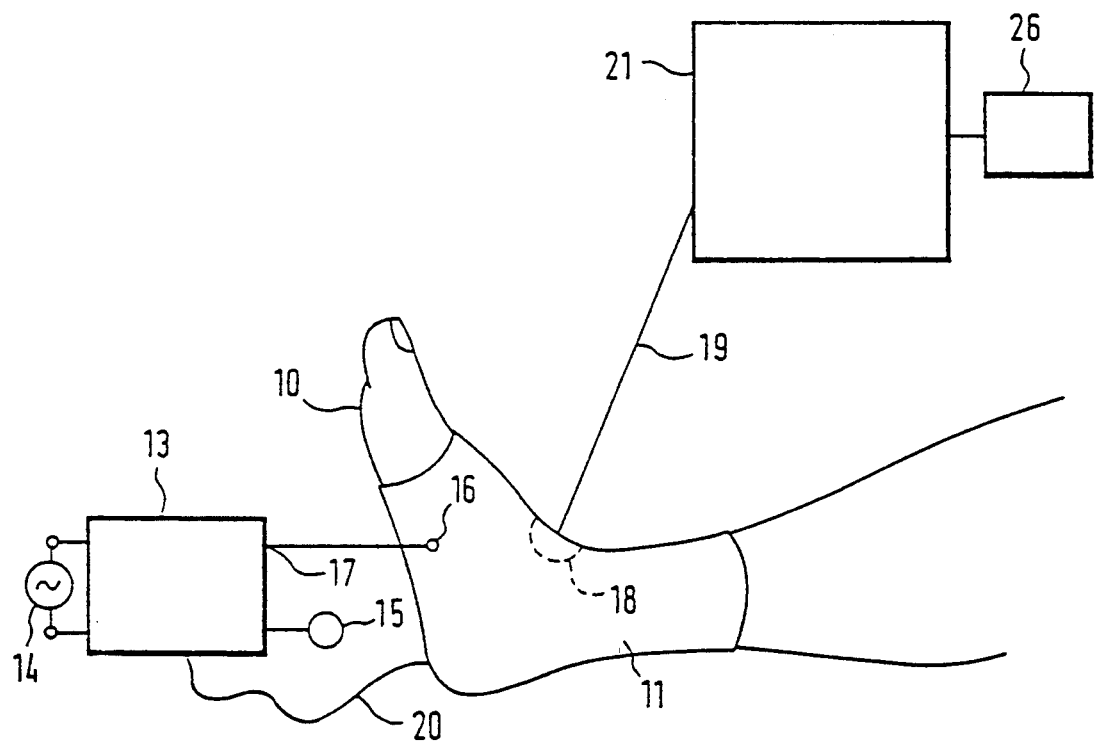

The invention will be explained in more detail in the following with reference to a description of an embodiment of the apparatus of the invention and also a description of a clinical investigation with reference to the accompanying drawings. In the drawings are shown:

FIG. 1 a schematic illustration of the apparatus of the invention,

FIG. 2 a graphic illustration of the print-out of the computer of FIG. 1,

FIGS. 3a to 3c tabelled results of the clinical investigation of 40 subjects and indeed with regard to the measured hyperthermal perfusion-latency, initial perfusion values and maximum perfusion values together with their significances in the Wilcoxon test and also in the Chi-Square test shown in brackets, FIGS. 4a to 4c graphic illustrations of the percent median differences of the three parameters hyperthermal perfusion-latency, initial perfusion values and maximum perfusion values which were determined during the investigation, and FIG. 5 a schematic illustration of an alternative apparatus in accordance with the invention.

FIG. 1 shows an extremity of a subject in the form of his right foot 10 which is covered over with a heated blanket 11 in the ankle region. The heated blanket 11 is folded around the foot, it could however also be a simple blanket or a heated cushion. The heated blanket is electrically heated with the electrical energy for heating the heating blanket being supplied to the heated blanket via a control circuit 13 and a cable 20. The control circuit 13 is connected to the mains 14 and has a desired value input 15 to which a reference value is supplied corresponding to the desired temperature of the heated blanket 11, in the present example 44° C. The actual temperature of the heated blanket which is determined by a temperature sensor 16 is applied to an actual value input 17 of the control circuit 13. A temperature probe 18 for determining the skin temperature of the patient is applied directly to the skin of the subject beneath the heated blanket at the position where it is folded over. The temperature determined by the temperature probe 18 is applied via a lead 19 to an evaluation computer 21.

The temperature probe has a measuring head with a diameter of approximately 3 cm and in the middle a small hole. There the laser probe 23 of a known laser perfusion measuring apparatus 24 is placed. The basic methodology of laser perfusion measurement is described in numerous investigations (see for example Shepherd AP, Riedel GL (1982) Continuous measurement of intestinal mucosal bloodflow by Laser-Doopler Velocimetry. Am J Physiol 242: G699–G672; Stern MD, Lappe DL, Bown PD, Chimosky JE, Holloway GA, Keiser HR (1977) Continuous measurement of tissue blood flow by Laser-Doppler-Spectroscopy. Am J Physiol 232: H441–H448; and Svensson H, Svedman P, Holmberg J, Wieslander JB (1983). Continuous monitoring of circulation in flaps. Transactions of the VIII International Congress of plastic surgery, Montreal, June 26–July 1). The principle of this investigation relates to a Doppler effect which is influenced, on the one hand, by the capillary hematokrit and, on the other hand, by the mean flow speed of the particles in the capillary region. These two determining parameters are computered into a "perfusion unit" via a computer evaluation. The computer which is used for this is accommodated in the laser perfusion measuring apparatus 24. In the present case a PeriFlux PF3 apparatus of the company Perimed in Sweden was used for carrying out a perfusion measurement. This apparatus is described in U.S. Pat. No. 4,590,948. The temperature probe is a component of the PeriFlux apparatus and is normally used to determine the temperature at the measuring location and to keep it constant via a heating device and a regulating circuit in order to avoid measurement falsifications. In the present case the probe was merely used to measure the temperature.

The measurement values determined from the laser perfusion measuring apparatus 24 "perfusion units" were likewise supplied to the computer 21 via the lead 25.

The computer establishes for each subject a protocol in the form of a computer graphic display showing the changes in the perfusion values which have been found in the form of a percentage of the initial value as a function of time in seconds from an increase in temperature of the subject as a result of the action of the heated blanket. This computer graphic display is printed out via a printer 26. The increase in skin temperature is computed as a result of a mean value formation by the computer. The time which is important for the present invention, the so-called hyperthermal perfusion-latency is the time from the start of the increase in skin temperature, which is caused by the heated blanket at the foot, up to the start of the increase in perfusion as a result of the increased skin temperature. The increase in perfusion is also determined by the computer by mean value formation, with only the values being shown in the graphic display from the determined increase onwards, in order to simplify the picture for the doctor carrying out the treatment. The protocol of FIG. 2 shows a curve A which applies for a healthy patient and as curve C the measured increase in skin temperature. All patients for which curves are found which lie on the left hand side of a curve A can be classified as healthy. If however, the curve found for a specific patient lies to the right hand side of the curve A, for example the curve B then this patient suffers from a polyneuropathy. The degree of the polyneuropathy can be determined as a result of the hyperthermal perfusion-latency which has been found. In the present example the hyperthermal perfusion-latency lies at 190 seconds in comparison with a value of less than 60 seconds for a healthy patient. With very severe polyneuropathy syndrome no increase in the perfusion can be found at all, the hyperthermal perfusion-latency is therefore also not measurable since the perfusion remains at the initial level. The determination that the perfusion has not increased is however itself a confirmation that a polyneuropathy syndrome of the most severe degree is already present.

The course of a measurement is as follows. First of all the heating up of the heated blanket to 44° C. is started by closing a switch (not shown). In parallel thereto the laser Doppler flowmetry measurement is started. The measurement is carried out for a time period of up to 10 minutes and skin temperatures up to 38° are reached. In carrying out the measurement foot movements of the patient must be avoided as far as possible since these lead to perfusion changes. Accordingly the curve determined by the computer must eventually be judged taking account of movement artifacts. These artifacts appear as peak values and are sorted out by the computer and ignored during the mean value formation. After determining the curve the hyperthermal perfusion-latency can then be measured on this curve.

In order to more clearly portray the clinical background to the invention the result of a clinical investigation of 40 persons will now be 40 persons were subdivided in accordance with their clinic into four subgroups which are set forth in the following: Group 1 included 10 healthy subjects (5 men and 5 women) which served as a control collective. In group 2 there were 10 patients (6 men, 4 women) which had suffered for at least three years from an orally treated diabetis mellitus and which sensed frequent or continuous paresthesia, but which were however completely unremarkable from their neurological status. Having regard to the known basic disease and the typical anamnesis it had to be assumed that these complaints represent the start of a PNS ("burning feet syndrom"). Group 3 was recruited from a further 10 subjects (7 men, 3 women) which had likewise suffered for at least 3 years from diabetis mellitus. These nine were set up with an oral antidiabetic medication, one subject was taking insulin. In contrast to group 2 all patients of this collective had pronounced disturbances of the lower extremities in the area of depth sensitivity and surface sensitivity which could be determined in the neurological status and could be reproduced at any time. In order to preclude a motoric participation a measurement of the nerve conduction speed and of the distal latency of the nervus peronaeus of the more strongly affected extremity was carried out electroneurographically. The incorporation into this group only took place when the nerve conduction speed lay in the normal region, that is above 41 m/sec. 10 subjects (8 men, 2 women) were combined into the fourth group who showed motoric failures in addition to sensitivity disturbances. These were verified electroneurographically with reference to a slowed nerve conduction speed of the nervus peronaeus, likewise at the more strongly effected lower extremity. Of the subjects 8 received oral antidiabetica, the remaining two were taking insulin.

Methodology

In all subjects the microcirculation of the skin was measured at the more strongly effected lower extremity and observed over a period of 5 minutes. At the same time the skin temperature was increased by means of a special probe which had been heated to 44° C. and the increase in microcirculation which could be observed was followed with the previously described laser perfusion measurement.

For the statistical evaluation the period from the start of the hyperthermia up to the occurrence of an increase in the microcirculation was used. This period was termed the so-called "hyperthermal perfusion-latency". Moreover, the initial perfusion value and the maximum value of the microcirculation were determined.

As a significance test there was used, on the one hand, the parameter-free method of Wilcoxon (see for example the book Guilford JP (1959) Fundamental Statistics in Psychology and Education. McGraw-Hill, New York: 587–588) and, on the other hand, the Chi-Square-Test which is likewise described in this book for checking variance differences. In accordance with the Wilcoxon test the significance lower limit was determined with $p \leq 0.02$. The minimum for the Chi-Square-Text was anchored at $p \leq 0.001$.

Results 40 persons (26 men, 14 women) were included in the investigation. The maximum age lay in all groups between 55 and 70 years with a relatively large scatter. Significant distinctions were not present between the two tests that were used. In all healthy subjects (group 1) the perfusion rose in median after 26 seconds. The median of the hyperthermal perfusion-latency lay in group 2 at 64, in group 3 at 180 and in group 4 at 235 seconds. The groups 1 to 3 are distinguished in the Wilcoxon test with a significance of $p \leq 0.01$, the significance between sensory and motoric PNS (groups 3 and 4) amounted to $p \leq 0.02$. All four groups had p values of less than $\leq 0.0001$ in the Chi-Square-Test whereby a very good differentiation of the group values is possible.

The initial perfusion values overlapped strongly in the investigated collectives which also led to no significance in accordance with the Chi-Square-Test. The best differences in this respect were obtainable between groups 1 and 4, i.e. between the two extreme groups, however P with a value of 0.0016 still lay above the required limit of $P \leq 0.001$ for the Chi-Square-Test. In accordance with the Wilcoxon test the distinction in these two groups with $p \leq 0.01$ was highly significant whereby it is documented that the most severe form of PNS which was to be found in this study lay in the perfusion distribution clearly below the sound control group. However an association of the individual value to the respective group is statistically not possible.

The maximum perfusion values show considerably lower values from group 3 onwards. Both groups are distinguished highly significantly with $p \leq 0.01$ from the control group and from group 2 in the Wilcoxon test. In the Chi-Square-Test $P \leq 0.0001$. Between groups 1 and 2 and also 3 and 4 the significant maximum perfusion distinctions could not be found either in the Wilcoxon test or in the Chi-Square-Test.

A further differentiation into male and female subgroups brought no additional viewpoints.

The tables 1–3 of FIGS. 3a to 3c represent hyperthermal perfusion-latency, initial perfusion values and maximum perfusion values with their significances in the Wilcoxon test and also in the Chi-Square-Test in brackets. The graphs 1 to 3 of FIGS. 4a to 4c show the percentage median distinctions of the three parameters.

Discussions

The results of this investigation clearly indicate that the provocation of the microcirculation by hyperthermia shows distinctions in the stages of the PNS syndrom. Above all the hyperthermal perfusion-latency is well suited for differentiation. The normal collective can be limited upwardly with hyperthermal perfusion-latency values up to 50 seconds. A comparison of the individual data for group 2 shows that seven of the ten subjects with Burning-Feet-Syndrom lay above this value, this signifies that three subjects had no pathologically delayed hyperthermal perfusion-latency. On the assumption that actually all subjects of this group had their complaints in the region of an incipient PNS this shows a sensitivity of 70% at this early stage. In the two groups with severe polyneuropathic changes not a single subject had a hyperthermal perfusion-latency value below 50 seconds.

Notable is however not only the increasing slowed hyperthermal perfusion-latency in the individual groups but also the fact that the microcirculation increase in the two highest PNS groups reduces significantly with substantially identical initial values. Thus it seems apparent that the increase of the microcirculation in groups 3 and 4 could not be evaluated at all as a true increase but perhaps represents merely a forced greater microcirculation fluctuation caused by the hyperthermy. From some presently non-published results it appears that this is entirely probable, some persons appear only to reach the temperature which is required to induce a clear increase in microcirculation after 10 minutes or more. After 5 minutes of hyperthermy with a probe at 44° maximum skin temperatures of 36° are achieved, the further increase in temperature then takes place very slowly.

One must certainly consider that the stimulation of the microcirculation is a result of the autonomous nerve system but the differences of the hyperthermal perfusion-latency in the groups is clear and the frequency of the autonomic neuropathy has often been investigated and described in connection with motoric and sensory failures arising with polyneuropathy syndrome, or stated more precisely a separation into individual independent clinical neuropathy forms is practically impossible, it is also shown by the frequent attempts to classify this illness.

The hyperthermal laser Doppler flowmetry will certainly not be able to displace customary electroneurography in the diagnosis of motoric PNS and this was also not the object of this study. Rather this investigation technique makes it possible for the first time to carry out a routine diagnosis and differentiation of the individual stages of a PNS, and thus under some circumstances to objectively judge a possible therapeutic success. The diagnosis of a PNS is possible with the aid of hyperthermal laser Doppler flowmetry at a time when a treatment has better chances of success than at later stages.

FIG. 5 shows an alternative apparatus in accordance with the invention in which temperature values are measured insted of perfusion values.

The apparatus is in many respects very similar to the apparatus of FIG. 1 which is why the same reference numerals have been used for the same parts. The control circuit for the heated blanket is in particular identical with that of FIG. 1.

In principal the measurement arrangement is very similar, the laser probe 23 and also the laser perfusion measuring apparatus 24 are however not present and the temperature measurement probe which is used is insulated relative to the heating blanket 11 which surrounds it. The skin temperature derived from the temperature probe 18 is applied via the lead 19 as previously to a microcomputer 21 which records and stores the variation with time of the skin temperature and determines the rise time between specific temperatures from the variation which has been determined and found.

In other words the time is measured here in which the skin temperature increases when the heating blanket is heated. Above all temperature changes are suitable here in 1° to 2° steps from 30° C. upwards up to a maximum of approximately 36° C.

With light neuropathic changes it has been found, in accordance with the invention, that the time span for the increase in skin temperature from 34° to 36° is extended relative to healthy subjects. For severe polyneuropathic changes a prolongation of the time span between 32° and 34° is also found and for very severe forms of polyneuropathy the time span from 30° to 32° is also increased.

With the heated blanket used for the tests, which has a certain "warm-up time" until it has fully reached 44° C. the normal regions, i.e. for healthy subjects, are 50 seconds for 30° to 32°, 30 seconds for 32° to 34° and 25 seconds for 34° to 36°. More severe stages frequently do not reach 36° in a measurement period of up to 5 minutes and have for example a skin temperature latence of 100 seconds or more for 30° to 32°.

As a whole measurements have so far been carried out on approximately 100 patients and the correlations can be found with hyperthermal laser Doppler flowmetry, above all from 32° C. upwards. When skin temperature delays arise amongst these patients to a massive degree then it is found that with hyperthermal laser Doppler flowmetry no increase at all can any longer be achieved. Thus one can say that the method with the laser perfusion measurement is admittedly an earlier measurement but also a measurement which is more subject to disturbances. Muscular tensions cannot be precluded despite good software and are more likely to be included. With the temperature measurements they play hardly any role.

In more severe stages a better judgement is possible with the temperature method since here no increase can be found at all with the hyperthermal laser Doppler flowmetry and thus it is also not possible to measure any hyperthermal perfusion-latency. This is important above all for medication studies.

Finally it should be mentioned that in the embodiment of FIG. 5 the computer is also able to establish a protocol in the form of a computer graphic for each subject whereby comparisons can be represented between a specific patient and a normal patient or for a specific patient between the values found before and after treatment, and this computer graphic display can also be printed out via the printer 26.

The apparatus of FIG. 5 has the advantage that it can be manufactured at relatively favourable cost, since a relatively expensive perfusion measurement apparatus is not absolutely essential.

I claim:

1. A method of determining nerve damage (polyneuropathy) in a patient comprising the steps of:
   (a) with a heating device increasing the temperature of a skin portion on an extremity of the patient from a first temperature to above a second temperature;
   (b) monitoring the temperature of said skin portion;
   (c) taking a first time measurement when said second temperature is reached;
   (d) monitoring perfusion in the extremity at said skin portion while the temperature of said skin portion rises from the second temperature until a predetermined increase in perfusion is noted;
   (e) taking a second time measurement when said predetermined increase in perfusion is noted;
   (f) subtracting said first time measurement from said second time measurement to obtain a perfusion delay time; and
   (g) comparing this perfusion delay time with a previously established reference perfusion delay time;
   whereby a difference between the measured perfusion delay time in the patient and the previously established reference perfusion delay time is a measure of the presence and the extent of nerve damage in the patient.

2. A method according to claim 1 wherein the step of monitoring perfusion comprises the step of directing a laser beam onto said skin portion.

3. A method according to claim 1 wherein the step of taking a first time measurement is performed after the temperature of the skin portion has been raised by about 1° C. since the commencement of the heating step.

4. A method according to claim 1 including the step of determining the change in perfusion from the commencement of the perfusion monitoring step, and discontinuing the perfusion monitoring step when the monitored perfusion has changed by at least about 10%.

5. A method according to claim 4 wherein the discontinuing step is performed when the monitored perfusion has changed by at least about 25%.

6. A method according to claim 1 including the step of establishing the reference perfusion delay time by performing steps (a) through (e) on a patient having no nerve damage, and subtracting said first time measurement from said second time measurement.

7. A method according to claim 6, wherein the step of establishing is performed on a plurality of patients having no nerve damage, and including the step of setting the reference perfusion delay time based on the results of the establishing step performed on said plurality of patients.

8. A method of determining nerve damage (polyneuropathy) in a patient comprising the steps of:
 (a) with a heating device increasing the temperature of a skin portion on an extremity of the patient;
 (b) monitoring the temperature of said skin portion;
 (c) taking a first time measurement when the temperature of said skin portion has reached to a first temperature;
 (d) monitoring perfusion in the extremity at said skin portion while the temperature of said skin portion rises from the first temperature until a predetermined increase in perfusion is noted;
 (e) taking a second time measurement when said predetermined increase in perfusion is noted;
 (f) subtracting said first time measurement from said second time measurement to obtain a perfusion delay time; and
 (g) comparing this perfusion delay time with a previously established reference perfusion delay time;
 whereby a difference between the measured perfusion delay time in the patient and the previously established reference perfusion delay time is a measure of the presence and the extent of nerve damage in the patient.

9. A method of determining nerve damage (polyneuropathy) of a patient comprising the steps of:
 with a heating device increasing the temperature of the skin at a first position on an extremity of the patient from a first temperature to a second temperature;
 monitoring the skin temperature at a second position on said extremity, said second position being insulated against direct heating by said heating device;
 measuring the amount of time that elapses while the skin temperature at said second position rises from the first temperature to the second temperature; and
 comparing the amount of time measured with a previously established time interval required to raise the temperature of the skin of another patient known to have no nerve damage from the first temperature to the second temperature;
 whereby a relationship between the measured amount of time and the previously established time interval is a measure of the presence and of the extent of nerve damage in said patient.

10. A method according to claim 9 including the step of commencing the measuring step after said heating device has reached a predetermined, desired temperature.

11. A method according to claim 10 wherein said predetermined temperature of the heating device is about 44° C.

12. A method according to claim 9 wherein said first and second temperatures are within the range of 30° C. and 36° C.

13. A method according to claim 12 including the step of establishing temperature sub-ranges of 30° C. to 32° C., 32° C. to 34° C., and 34° C. to 36° C., wherein the step of measuring comprises the step of measuring the amount of time that elapses while the skin temperature at the second position rises through at least one of said temperature sub-ranges, and wherein the step of comparing comprises the step of comparing the measured amounts of time for the skin temperature at said second location to rise through said temperature sub-ranges with previously established time intervals for raising the temperature of the skin of the other patient through like temperature sub-ranges.

* * * * *